United States Patent [19]
Yoshida

[11] Patent Number: 5,581,074
[45] Date of Patent: Dec. 3, 1996

[54] INSPECTION APPARATUS WITH STROBOSCOPE INTENSITY COMPENSATION FEATURES

[75] Inventor: Hajime Yoshida, Tokyo, Japan

[73] Assignee: Hajime Industries Ltd., Tokyo, Japan

[21] Appl. No.: 342,701

[22] Filed: Nov. 21, 1994

[30] Foreign Application Priority Data

Nov. 29, 1993 [JP] Japan .................................. 5-298265

[51] Int. Cl.$^6$ ......................................... G01J 1/32
[52] U.S. Cl. .............. 250/205; 250/559.4; 250/214 DC; 348/132
[58] Field of Search ..................... 250/205, 559.05, 250/559.07, 559.08, 559.4, 214 C, 214 DC, 214 PC, 223; 348/132, 131

[56] References Cited

U.S. PATENT DOCUMENTS

| 4,305,658 | 12/1981 | Yoshida ................... 356/23 |
| 4,446,481 | 5/1984 | Edamatsu et al. ............... 358/106 |
| 5,053,614 | 10/1991 | Yui et al. ................... 250/205 |
| 5,134,273 | 7/1992 | Wani et al. ................. 250/205 |
| 5,233,175 | 8/1993 | Latta et al. ................ 250/205 |
| 5,250,797 | 10/1993 | Sano et al. ................. 250/205 |

Primary Examiner—Edward P. Westin
Assistant Examiner—Stephen Calogero
Attorney, Agent, or Firm—Bauer & Schaffer

[57] ABSTRACT

A stroboscope is employed as the lighting source for a video camera, the output of which is converted into a signal from which a fault in the object scanned is detected. The stroboscope is controlled in response to a portion of the output voltage of the video camera to insure that the luminous energy is constant.

2 Claims, 3 Drawing Sheets

5,581,074

INSPECTION APPARATUS WITH STROBOSCOPE INTENSITY COMPENSATION FEATURES

BACKGROUND OF THE INVENTION

1. Field of the Invention

The present invention relates generally to inspection apparatus that detect the defects on an inspected object by the use of, for example, a stroboscope and, more particularly, is directed to an inspection apparatus that is equipped with a suitable stroboscope luminous energy correction function.

2. Description of the Prior Art

The stroboscope as an irradiation lamp, owing to its extremely short flash time period, has been used as the lighting device for tachometers from old times, or conventionally used to make static images of moving objects.

Further, during the recent years, the stroboscope is frequently used as the lighting device for inspection apparatus that utilize a video camera and a signal processor to detect the defects on moving objects.

FIG. 1 shows a block diagram of a conventional inspection apparatus that uses a stroboscope, a video camera, a signal processor and so on.

In FIG. 1, a belt conveyer 1 is a transfer means that conveys thereon inspected objects 2 in the direction indicated at A. With belt conveyer 1 in the middle, placed in counter facing manner are a light irradiation unit 3A and a light receiving unit 3B so that they provide a position detecting device 3 which detects the position of the inspected object 2 when the inspected object 2 arrives at a predetermined inspection position. When the inspected object 2 at the inspection position shields the light emitted from the light irradiation unit 3A, a position detection signal is generated from the light receiving unit 3B.

A power source 4B is the irradiation power source of a stroboscope 4. A flash unit 4A is placed to face downwards from an angle at above the conveyer 1, so that it irradiates the inspected object 2 which arrives at the inspection position. When the inspection position detection signal from the light receiving unit 3B is received, the stroboscope power source 4B drives the flash unit 4A of the stroboscope 4 so that the stroboscope flash unit 4A irradiates the inspected object 2 at the inspection position. The stroboscope 4 consists of the stroboscope power unit 4B and the stroboscope flash unit 4A.

A video camera 6 picks up the inspected object 2 that arrives at the inspection position and is irradiated by the stroboscope flash unit 4A. Video camera 6 is therefore placed above the belt conveyer 1 looking down so as not receive the light from the flash unit 4A directly. Signal processor 5 conducts the signal processing of the video signal from video camera 6 in order to detect the defects on the inspected object 2, when it receives the inspection position detection signal from the light receiving unit 3B.

The conventional inspection apparatus using such stroboscope as arranged above functions as following description. That is to say, even though the inspected object 2 is being conveyed on the conveyer 1, by the flashing characteristics of the stroboscope 4 that flashes within extremely short period of time, at the inspection area that receives the position detection signal from light receiving unit 3B, the video camera 6 picks up the object 2 as a practically static image.

Therefore, due to the flash characteristics of the stroboscope that flashes within an extremely short period of time, the defect detection quality deterioration of the inspected object due to its movement is eliminated, so that inspection of the inspected object is conducted with good precision.

However, at the inspection apparatus that use such conventional stroboscope, since the flash unit 4A of the stroboscope 4 normally use a Xenon tube, with long term use where its flashing numbers is great, as shown by a solid line curve C in FIG. 2, the luminous energy variation of the Xenon tube occurs, so that there was the inconvenience that the luminous energy thereof drops by the span of life of the Xenon tube.

Further, along with the improvement of the processing precision of the processor of signal processing, any variation in the luminous energy of the flash unit in the stroboscope, whether it be minor or small, there was the inconvenience that great influence is caused to the judgement precision of signal processing.

OBJECTS AND SUMMARY OF THE INVENTION

Accordingly, it is an object of the present invention to provide an inspection apparatus with stroboscope luminous energy correction functions so that the stroboscope luminous energy is always stabilized in order to maintain the judgement precision and stability of said inspection apparatus.

According to an aspect of the present invention, there is provided an inspection apparatus having a stroboscope luminous energy correction function, which comprises:

a conveyer means for conveying an inspected object;

a position detection means for detecting a position of the inspected object arriving at an inspection position to produce a position detection signal;

a stroboscope including a flash unit irradiating the inspected object at the inspection position and a power source supplying an electric power to the flash unit;

a video camera means for picking up the inspected object as irradiated by the flash unit of the stroboscope to produce a video signal of the inspected object;

a signal processing circuitry which processes the video signal of the inspected object as picked up by the video camera means upon reception of the position detection signal from the position detection means;

a photoelectric conversion means for converting a part of the light from the stroboscope flash unit into a voltage; and a luminous energy control means for controlling the luminous energy of the flash unit of the stroboscope to be constant in response to the voltage from the photoelectric conversion means.

BRIEF DESCRIPTION OF THE DRAWINGS

A better understanding of the objects, features and advantages of the present invention can be gained from a consideration of the following detailed description of the preferred embodiment thereof, in conjunction with the figures of the accompanying drawings, wherein.

DETAILED DESCRIPTION OF THE PREFERRED EMBODIMENT

The main object of the present invention lies in enabling maintenance of judgement precision and stability on an inspection apparatus, in spite of stroboscope flash luminous energy variations.

Figure 3:
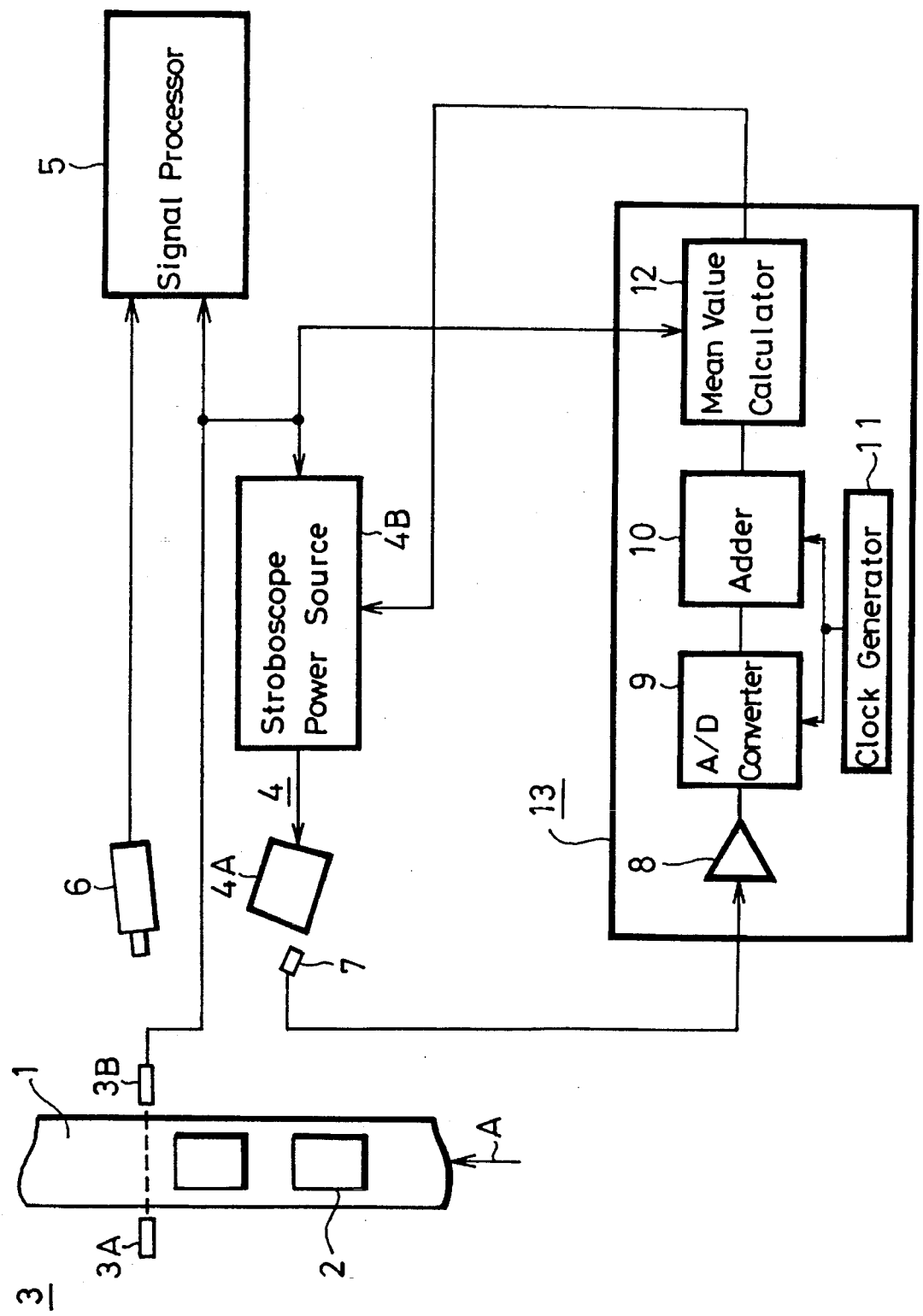
FIG. 3 is a block diagram showing an embodiment of the inspection apparatus that utilizes a stroboscope luminous energy correction control circuitry according to the present invention.

FIG. 3 is a block diagram showing the construction of an embodiment of the inspection apparatus with a luminous energy correction function of a flash lamp of a stroboscope according to the present invention. In FIG. 3, the like parts that correspond to those used in the inspection apparatus with the conventional stroboscope as shown in FIG. 1 are assigned with the same symbols, and detail explanations thereof will be omitted.

Figure 1:
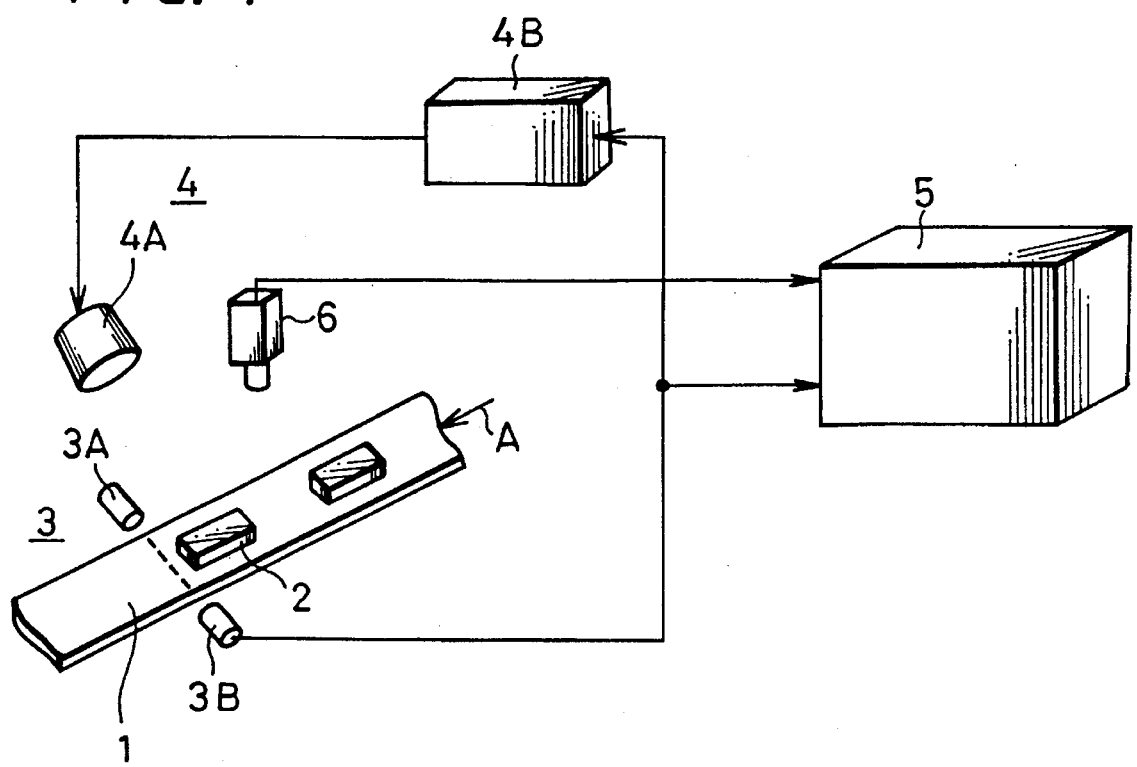
FIG. 1 is a block diagram showing a conventional inspection apparatus that uses a stroboscope.

The point of difference between the inspection apparatus that uses the luminous energy correction function according to the present invention, shown in FIG. 3, to such conventional inspection apparatus that uses the stroboscope shown in FIG. 1, is that a photoelectric conversion sensor 7 and a luminous energy correction control circuitry 13 are further installed on the conventional apparatus.

In FIG. 3, belt conveyer 1 is the means to convey thereon the inspected objects 2 in the arrow A direction. The light irradiating unit 3A and the light receiving unit 3B are place to be counter facing each other with the belt conveyer 1 there between, so that they form the inspection position detection device 3 that detects the fact that the inspected object 2 reaches the predetermined inspection position when the light from the light irradiating unit 3A is shielded by the inspected object 2 arrived at the predetermined inspection position.

The stroboscope power source 4B is the part that acts as the flash light source. The stroboscope flash unit 4A is placed above the conveyer 1 looking down at an angle so that it irradiates the inspected object 2 at the predetermined inspection position. The stroboscope power source 4B drives and flashes the stroboscope flash unit 4A when it receives the position detection signal from the light receiving unit 3B so that the stroboscope flash unit 4A irradiates the inspected object 2 at the inspection position. The stroboscope power unit 4B and the stroboscope flash unit 4A construct the stroboscope 4 similar to the prior art.

Video camera 6 picks up the inspected object 2 that is irradiated by the stroboscope flash unit 4A at the inspection position. The video camera 6 is positioned to look down from above the conveyer 1 so as to not receive the light from the flash unit 4A directly and also not to disturb the irradiation of flash unit 4A on the object 2. The signal processing circuitry 5 detects the defects on inspected object 2 by processing the image signal from video camera 6 when it receives the position detection signal from light receiving unit 3B.

In this example, the photoelectric conversion sensor 7 is placed at a position near the flash unit 4A so that it will detect a part of the irradiated light therefrom in a manner that it will not interfere with its irradiation onto the object 2 by the flash unit 4A. The output voltage of photoelectric conversion sensor 7 is amplified by an amplifier 8. The output voltage as amplified by amplifier 8 is converted to digital values by an A/D converter 9 and then added at an adder 10. The A/D converter 9 and adder 10 are supplied with their operation clock from a clock generator 11. The added output of a predetermined number of flashes of flash unit 4A from adder 10 is supplied to a mean value calculator 12. The mean value calculator 12 calculates a mean value of the predetermined number of flashes of the flash unit 4A. The mean value output from the mean value calculator 12 is supplied to the stroboscope power source 4B. The luminous energy correction control circuitry 13 of the stroboscope 4 is constructed by the above amplifier 8, A/D converter 9, adder 10, clock generator 11 and mean value calculator 12.

The operation of the inspection apparatus that has the luminous energy correction control function of the flash lamp according to the present invention will be explained hereunder.

Figure 4:
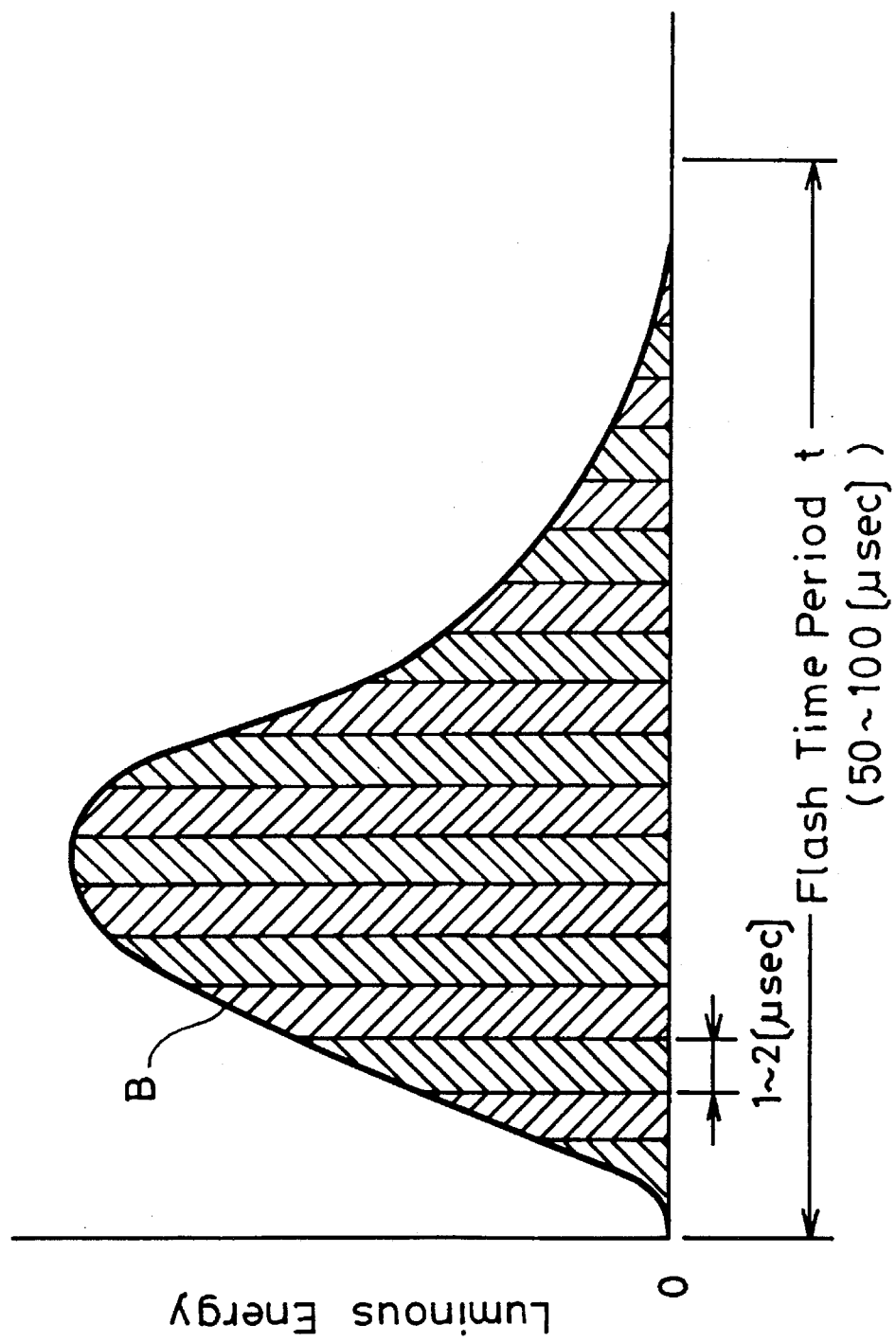
FIG. 4 is a graph in order to explain the functions of the embodiment of the inspection apparatus that utilizes the stroboscope luminous energy correction control circuitry of the present invention.

A part of the light at the time of each flash of the stroboscope 4 is converted into an analog electrical signal by the photoelectric conversion sensor 7 and is supplied to the amplifier 8. The amplified analog electrical signal by the amplifier 8 is supplied to the A/D converter 9 and is converted into the electrical signal of digital values. In this case, the A/D conversion is conducted in a manner that, as shown in FIG. 4, the luminous energy of the stroboscope flash unit 4A in its one flash time period t is divided in a predetermined number of values by the clock frequency from the clock generator 11. Then, the divided luminous energies are added or integrated by the adder 10. The added values of the predetermined number of flashes are averaged by the mean value calculator 12 and the mean value therefrom is supplied to the stroboscope power source 4B, whereby the luminous energy of the flash unit 4A is stabilized or made constant. The reason why the integrated value of each flash wave of the stroboscope flash unit 4A is calculated is that the flash wave is different dependent on luminous energy and shape of the stroboscope flash unit 4A such as helical shape, ring shaped or straight shape, or the internal structural by makers. For such reason, the simply described luminous energy may contain differences of energy within the flash time period depending upon the flash wave forms.

The flash wave shown by curve B in FIG. 4 is a typical example of the flash wave at the time of the stroboscope flash in helical form. In FIG. 4, its flash period time t is 50–100 micro seconds. The clock frequency of the clock generator 11 that divides the flash luminous energy from the stroboscope flash unit 4A in the flash period time t by the A/D conversion is 1–2 micro seconds.

As described above, since the stroboscope flash waveform is such the curve B as shown in FIG. 4, it is necessary to obtain the accurate value of luminous energy by accumulating the same along the curve B. Therefore, as shown in FIG. 4, by dividing the flash waveform into several portions of values with time, such values are added to obtain the integrated value.

In FIG. 4, a rough division is shown for explanation purposes, but it is needless to say that the finer the division for integration is, the better is the precision. In order to obtain the practical precision, 50–100 divisions are desirous. In this case, if the precision may be lowered, the division number may be reduced.

Further, the reason for obtaining such mean value of the integrated values of the predetermined number of flash waveforms is that, the stroboscope luminous energy of the flash does not drastically change within a short time period, and further, rather than checking the luminous energies at times, obtaining the mean value of successive some numbers of flashes serves to absorb the delicate variation of each individual flash, so that a function with good precision can be obtained.

The values to be averaged may be within a practical range, such as 10 or 100 times of flashes that can be selected at random. This value is the number of flashes so that the position detection signal from the light receiving unit 3B is supplied to the mean value calculator 12 to control the same by number of flashes.

Figure 2:
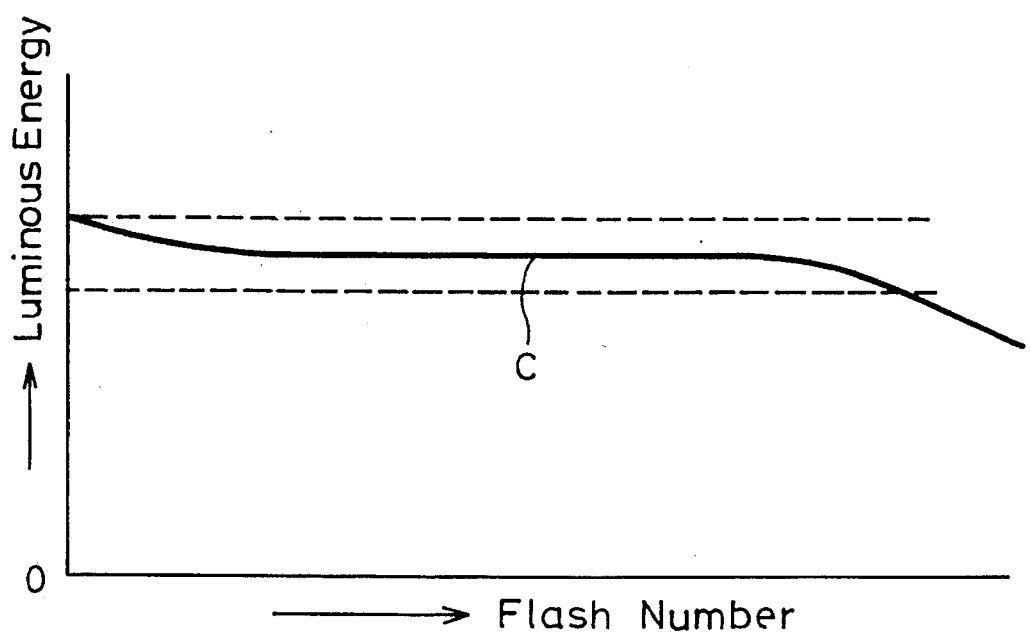
FIG. 2 is a life time curve that shows the relation between the stroboscope flash number and the luminous energy thereof.

The digital output from the mean value calculator 12 is supplied to the stroboscope power source 4B to thereby control the flash luminous every of the stroboscope flash unit 4A. Control of the stroboscope flash is normally conducted by varying the capacity of the charging capacitor of the unit 4A or the voltage value at the high voltage power source. If such a stroboscope on the market that has a special external terminal for controlling the flash luminous energy is used, the above can be realized with easy. Normally, the external terminals for luminous energy control conduct control by providing digital values of 3–6 bits. At such normal control, as shown by the broken line range in FIG. 2, since the actual variation width of the luminous energy of the flash lamp remains within a range of few percent, the control bit number can be determined as necessary so that 3 bit control makes practical use possible.

According to the above mentioned example, there is provided the luminous energy correction control circuitry 13 in which the luminous energy of stroboscope flash unit 4A is measured by the voltage from photoelectric converter 7, the integrate value of the flash luminous energy within the flash time period t of the flash unit 4A is calculated, thereafter the mean value of the predetermined number of flashes can be calculated, and then the mean value of the flash luminous energy is supplied to the stroboscope power source 4B, whereby the luminous energy variations of stroboscope flash unit 4A are corrected. Therefore, the luminous energy of the flash unit 4A can always be made constant to enable the judgement precision and stability maintenance of the inspection apparatus.

According to the present invention, there is provided the luminous energy correction control means in which the flash luminous energy of the stroboscope flash unit is measured from the voltage from the photoelectric conversion means, the integrated value of flash luminous energy of a preset number within the flash time period of the stroboscope flash unit is calculated, thereafter the mean value of luminous energies of the predetermined number of flashes is calculated and the mean value of flash luminous energies is supplied to the stroboscope power source, whereby the fluctuation of luminous energy of the stroboscope flash unit is corrected. Therefore, the luminous energy from the stroboscope flash unit is regularly stabilized to keep maintenance of judgement precision and stability at the inspection apparatus.

According to the present invention, as above mentioned, the luminous energy correction control means is constructed by the A/D converter that converts the voltage of photoelectric conversion means into digital values, the adder that adds the output voltage from the A/D converter, the clock generator that supplies clock to the A/D converter and the adder, and the mean value calculator that obtains the mean value from the adder outputs, so that the luminous energy of the stroboscope flash unit is regularly stabilized in order to positively maintain judgement precision and stability of the inspection apparatus.

It should be understood that the above description is presented by way of example on the preferred embodiment of the invention and it will be apparent that modifications and variations thereof could be effected by one with ordinary skill in the art without departing from the spirit and scope of the novel concepts of the invention so that the scope of the invention should be determined only by the appended claims.

I claim as my invention:

1. An inspection apparatus having a stroboscope luminous energy correction function, comprising:

a conveyor means for conveying an inspected object;

a position detection means for detecting the position of said inspected object arriving at an inspection station to produce a position detection signal;

a stroboscope including a flash unit having a luminous energy, producing light irradiating said inspected object at the inspection station and a power source supplying an electric power to said flash unit;

a video camera means for picking up said inspected object as irradiated by said flash unit of the stroboscope to produce a video signal of said inspected object;

a signal processing circuitry which processes the video signal of said inspected object as picked up by said video camera means upon reception of said position detection signal from said position detection means;

a photoelectric conversion means for converting a part of the light from said stroboscope flash unit into a voltage; and a luminous energy control system for controlling the luminous energy of the flash unit of said stroboscope to be constant in response to the voltage from said photoelectric conversion means, said luminous energy control system having an A/D converter means, a clock generator means, an adder means, and a mean value calculator means, said A/D converter means converting the luminous energy of the flash unit of said stroboscope to a predetermined number of digital values on tho basis of a clock from said clock generator means and supplying the same to said adder means, said adder means integrating the same predetermined number of outputs from said A/D converter means based on the clock from said clock generator means, and said mean value calculator means averaging a predetermined number of outputs from said adder means and supplying a mean value therefrom to said power source of said stroboscope.

2. The inspection apparatus as claimed in claim 1, in which said mean value calculator means obtains a mean value of integrated values of luminous energies of successive numbers of flashes of said flash unit to thereby control the luminous energy of said flash unit substantially constant.

* * * * *